(12) United States Patent
Govari et al.

(10) Patent No.: US 9,345,533 B2
(45) Date of Patent: *May 24, 2016

(54) CATHETER WITH BENDABLE TIP

(75) Inventors: Assaf Govari, Haifa (IL); Andres Claudio Altmann, Haifa (IL); Ariel Garcia, Duarte, CA (US)

(73) Assignee: Biosense Webster, Inc.

( * ) Notice: Subject to any disclaimer, the term of this patent is extended or adjusted under 35 U.S.C. 154(b) by 50 days.

This patent is subject to a terminal disclaimer.

(21) Appl. No.: 13/470,871

(22) Filed: May 14, 2012

(65) Prior Publication Data

US 2013/0131663 A1    May 23, 2013

Related U.S. Application Data

(62) Division of application No. 12/134,592, filed on Jun. 6, 2008, now Pat. No. 8,437,832.

(51) Int. Cl.
*A61B 18/14* (2006.01)
*A61B 5/05* (2006.01)
*A61B 19/00* (2006.01)
*A61M 25/00* (2006.01)

(52) U.S. Cl.
CPC . *A61B 18/14* (2013.01); *A61B 5/05* (2013.01); *A61B 18/1492* (2013.01); *A61B 2019/4857* (2013.01); *A61M 25/0082* (2013.01); *A61M 2025/0081* (2013.01); *Y10T 29/49826* (2015.01)

(58) Field of Classification Search
CPC .................. A61B 2018/00357; A61B 18/1492
USPC ........ 606/32, 41, 47; 600/374, 139, 141–143, 600/145, 146, 149, 150; 607/119
See application file for complete search history.

(56) References Cited

U.S. PATENT DOCUMENTS

| | | |
|---|---|---|
| 3,841,150 A | 10/1974 | Pearson |
| 3,971,364 A | 7/1976 | Fletcher |
| 4,764,114 A | 8/1988 | Jeffcoat et al. |
| 4,856,993 A | 8/1989 | Maness |
| 4,930,494 A | 6/1990 | Takehana et al. |
| 5,263,493 A | 11/1993 | Avitall |
| 5,368,564 A | 11/1994 | Savage |

(Continued)

FOREIGN PATENT DOCUMENTS

| | | |
|---|---|---|
| DE | 19750441 | 6/1999 |
| EP | 928601 A1 | 7/1999 |

(Continued)

OTHER PUBLICATIONS

Okumura, Y. et al. A Systematic Analysis of In Vivo Contact Forces on Virtual Catheter Tip-Tissue Surface Contact During Cardiac Mapping and Intervention. J of Cardiovasc Electrophysiol, vol. 19, pp. 632-640, Jun. 2008.

(Continued)

*Primary Examiner* — Michael Peffley
*Assistant Examiner* — Thomas Giuliani

(57) ABSTRACT

A medical probe includes a flexible insertion tube, having a distal end for insertion into a body cavity of a patient, and a distal tip, which is disposed at the distal end of the insertion tube and is configured to be brought into contact with tissue in the body cavity. A coupling member couples the distal tip to the distal end of the insertion tube and includes a tubular piece of an elastic material having a helical cut therethrough along a portion of a length of the piece.

4 Claims, 2 Drawing Sheets

(56) References Cited

U.S. PATENT DOCUMENTS

| | | |
|---|---|---|
| 5,391,199 A | 2/1995 | Ben-Haim |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A * | 3/1998 | Laske et al. .................. 607/122 |
| 5,769,843 A | 6/1998 | Abela |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella |
| 5,947,320 A | 9/1999 | Bordner et al. |
| 5,964,757 A | 10/1999 | Ponzi |
| 5,974,320 A | 10/1999 | Ward |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 * | 6/2001 | Fleischman ........ A61B 18/1492 600/374 |
| 6,266,551 B1 | 7/2001 | Osadchy et al. |
| 6,272,371 B1 * | 8/2001 | Shlomo .................... A61B 5/06 128/899 |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy |
| 6,351,549 B1 | 2/2002 | Souluer |
| 6,398,738 B1 | 6/2002 | Millar |
| 6,436,059 B1 | 8/2002 | Zanelli |
| 6,456,864 B1 | 9/2002 | Swanson |
| 6,484,118 B1 | 11/2002 | Govari |
| 6,551,302 B1 | 4/2003 | Rosinko |
| 6,569,098 B2 | 5/2003 | Kawchuk |
| 6,574,492 B1 | 6/2003 | Ben-Haim |
| 6,584,856 B1 | 7/2003 | Biter |
| 6,602,242 B1 | 8/2003 | Fung et al. |
| 6,612,992 B1 | 9/2003 | Hossack |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas |
| 6,973,339 B2 | 12/2005 | Govari |
| 6,997,924 B2 | 2/2006 | Schwartz |
| 7,077,823 B2 | 7/2006 | McDaniel |
| 7,156,816 B2 | 1/2007 | Schwartz |
| 7,235,070 B2 | 6/2007 | Vanney |
| 7,297,116 B2 | 11/2007 | Varghese et al. |
| 7,306,593 B2 | 12/2007 | Keidar |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari |
| 7,604,605 B2 | 10/2009 | Zvuloni |
| 7,662,151 B2 * | 2/2010 | Crompton, Jr. ........ A61B 18/14 606/41 |
| 7,681,432 B2 | 3/2010 | Hay |
| 7,686,767 B2 | 3/2010 | Maschke |
| 7,911,315 B2 | 3/2011 | Bradley |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,357,152 B2 * | 1/2013 | Govari et al. .................. 606/41 |
| 8,374,819 B2 | 2/2013 | Govari et al. |
| 8,535,308 B2 * | 9/2013 | Govari et al. .................. 606/41 |
| 8,900,229 B2 * | 12/2014 | Govari et al. .................. 606/41 |
| 8,926,528 B2 | 1/2015 | Govari et al. |
| 9,033,916 B2 | 5/2015 | Schultz |
| 2001/0047129 A1 | 11/2001 | Hall |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0068931 A1 | 6/2002 | Wong et al. |
| 2002/0087089 A1 | 7/2002 | Ben-Haim |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 * | 4/2004 | Sommer ........................ 600/374 |
| 2004/0068178 A1 | 4/2004 | Govari |
| 2004/0097806 A1 | 5/2004 | Hunter et al. |
| 2004/0102769 A1 | 5/2004 | Schwartz |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono |
| 2006/0009735 A1 | 1/2006 | Viswanathan |
| 2006/0015096 A1 | 1/2006 | Hauck |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo |
| 2006/0247618 A1 | 11/2006 | Kaplan et al. |
| 2006/0276703 A1 | 12/2006 | Fuimaono et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 * | 5/2007 | Paul .................... A61B 18/1492 606/41 |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167804 A1 | 7/2007 | Park |
| 2007/0167818 A1 | 7/2007 | Osborn et al. |
| 2007/0167819 A1 | 7/2007 | Osborn et al. |
| 2007/0179492 A1 | 8/2007 | Pappone |

(56) References Cited

U.S. PATENT DOCUMENTS

| | | |
|---|---|---|
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1* | 6/2008 | Magnin et al. ............ 600/437 |
| 2008/0161796 A1* | 7/2008 | Cao .................. A61B 18/1492 606/41 |
| 2008/0183075 A1 | 7/2008 | Govari |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsummura |
| 2008/0275428 A1 | 11/2008 | Tegg et al. |
| 2008/0275442 A1 | 11/2008 | Paul et al. |
| 2008/0275465 A1 | 11/2008 | Paul |
| 2008/0281319 A1 | 11/2008 | Paul |
| 2008/0287777 A1 | 11/2008 | Li |
| 2008/0288038 A1 | 11/2008 | Paul |
| 2008/0294144 A1 | 11/2008 | Leo |
| 2008/0294158 A1* | 11/2008 | Pappone ............ A61B 18/1492 606/41 |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein |
| 2010/0152574 A1 | 6/2010 | Erdman |
| 2010/0160770 A1 | 6/2010 | Govari et al. |
| 2010/0160778 A1 | 6/2010 | Eskandari et al. |
| 2010/0168620 A1 | 7/2010 | Klimovitch |
| 2010/0168918 A1 | 7/2010 | Zhao et al. |
| 2010/0274239 A1 | 10/2010 | Paul et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0152880 A1 | 6/2011 | Alvarez et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 | 2/2005 |
| EP | 1586281 A1 | 10/2005 |
| EP | 1690564 | 8/2006 |
| EP | 1743575 | 1/2007 |
| EP | 1897581 | 8/2007 |
| EP | 2127604 | 6/2008 |
| EP | 2000789 A2 | 12/2008 |
| EP | 2 047 797 A2 | 4/2009 |
| EP | 1820464 | 4/2009 |
| EP | 2338411 | 9/2009 |
| EP | 2130508 B1 | 12/2009 |
| EP | 2338412 | 12/2009 |
| EP | 2196143 A1 | 6/2010 |
| EP | 2305115 A1 | 4/2011 |
| EP | 2172240 B1 | 12/2012 |
| JP | 8243168 A | 9/1996 |
| JP | 8266486 A | 10/1996 |
| JP | 2000126301 A | 5/2000 |
| JP | 2000508224 A | 7/2000 |
| JP | 2005237964 A | 9/2005 |
| JP | 2005345215 A | 12/2005 |
| JP | 2006255401 A | 9/2006 |
| JP | 2007181696 A | 7/2007 |
| JP | 2005345215 | 4/2010 |
| JP | 2006064465 | 6/2011 |
| WO | 94/17856 A1 | 8/1994 |
| WO | WO 95/10326 | 4/1995 |
| WO | WO 96/05768 | 2/1996 |
| WO | WO 97/29678 | 8/1997 |
| WO | WO 97/29709 A | 8/1997 |
| WO | WO 97/29710 A | 8/1997 |
| WO | WO 98/29032 A | 7/1998 |
| WO | WO 03/020139 | 3/2003 |
| WO | 2006/043884 A1 | 4/2006 |
| WO | WO 2006/086152 A2 | 8/2006 |
| WO | WO 2006/092563 A1 | 9/2006 |
| WO | WO 2006/135483 A2 | 12/2006 |
| WO | WO 2007/015139 A2 | 2/2007 |
| WO | WO 2007/025230 | 3/2007 |
| WO | WO 2007/098494 | 3/2007 |
| WO | WO 2007/050960 | 5/2007 |
| WO | WO 2007/067938 | 6/2007 |
| WO | WO 2007/076312 A2 | 7/2007 |
| WO | WO 2007/082216 | 7/2007 |
| WO | WO 2007/111182 | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 | 7/2009 |
| WO | WO 2009/147399 | 12/2009 |
| WO | WO 2010/008975 | 1/2010 |
| WO | WO 2011/046874 A1 | 4/2011 |

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

Biter, William J. et al., "Magnetic Wire for Monitoring Strain in Composites", *Sensors*, Jun. 2001, www.sensormag.com, pp. 110-114.

Partial European Search Report mailed on Dec. 7, 2009 from corresponding European Patent Application No. 09251502.2.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

(56) References Cited

OTHER PUBLICATIONS

Instron Marketing Brochure, "Medical Device Testing Systems", Instron 2007 http://web.archive.org/web/20080318092822/http://www.instron.com.tr/wa/library/streamfile.aspx?doc=1678&download=true.

Instron, "Series 3300 Load Frames, Reference Manual Equipment", Instron, pp. 1-5 and 1-10, 2004.

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Peirs, J. et al., "Design of an Optical Force Sensor for Force Feedback during Minimally Invasive Robotic Surgery", Eurosensors XVII, 2003, pp. 1063-1066, http://mech.kuleuven.be/micro/pub/medic/Paper_Eurosensors_2003_MIS_sensor_extended.pdf.

Partial European Search Report mailed on Sep. 18, 2009 from related European Patent Application No. 08253265.6.

European Search Report mailed on Mar. 8, 2010 from related European Patent Application No. 09252143.4.

Partial European Search Report mailed on Mar. 29, 2010 from related European Patent Application No. 09252879.3.

European Search Report mailed on Mar. 2, 2011 from related European Patent Application No. 10175931.4.

European Search Report mailed on Mar. 28, 2011 from related European Patent Application No. 10252189.5.

European Search Report mailed on Mar. 30, 2011 from related European Patent Application No. 10252020.2.

European Search Report mailed on May 16, 2011 from related European Patent Application No. 10252232.3.

European Search Report mailed on Aug. 5, 2011 from related European Patent Application No. 11158804.2.

European Search Report mailed on Sep. 20, 2011 from related European Patent Application No. 11250066.5.

European Search Report mailed on Sep. 23, 2011 from related European Patent Application No. 11169251.3.

European Search Report mailed on Oct. 28, 2011 from related European Patent Application No. 11171842.5.

European Search Report mailed on Nov. 17, 2011 from related European Patent Application No. 11177600.1.

European Search Report mailed on Feb. 15, 2012 from related European Patent Application No. 11182854.7.

European Search Report mailed on May 2, 2012 from related European Patent Application No. 11189326.9.

European Search Report mailed on Jun. 4, 2012 from related European Patent Application No. 12163784.7.

European Search Report mailed on Jul. 20, 2012 from related European Patent Application No. 12161784.9.

European Search Report mailed on Nov. 20, 2012 from related European Patent Application No. 12176163.9.

European Search Report mailed on Feb. 11, 2013 from related European Patent Application No. 11187525.8.

European Search Report mailed on Apr. 9, 2013 from related European Patent Application No. 13150145.4.

* cited by examiner

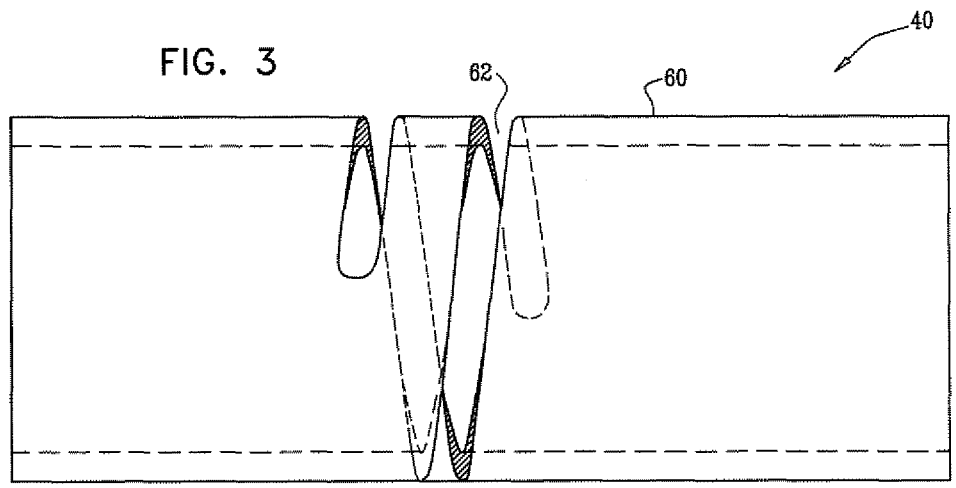

CATHETER WITH BENDABLE TIP

CROSS REFERENCE TO RELATED APPLICATIONS

This application is a divisional application of U.S. Ser. No. 12/134,592, filed Jun. 6, 2008, now U.S. Pat. No. 8,437,832, the contents of which are hereby incorporated herein by reference.

FIELD OF THE INVENTION

The present invention relates generally to invasive medical devices, and specifically to the construction of probes for insertion into body organs.

BACKGROUND OF THE INVENTION

In some diagnostic and therapeutic techniques, a catheter is inserted into a chamber of the heart and brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

SUMMARY OF THE INVENTION

The embodiments of the present invention that are described hereinbelow provide a novel design of an invasive probe, such as a catheter. The probe comprises a flexible insertion tube, having a distal end for insertion into a body cavity of a patient. The distal tip of the probe is coupled to the distal end of the insertion tube by a coupling member. The coupling member comprises a tubular piece of an elastic material, such as a superelastic alloy, with a helical cut running along a portion of the length of the piece.

The coupling member permits the distal tip to bend in response to pressure exerted on the distal tip when the distal tip engages tissue in the body cavity. Typically, the bend angle is proportional to the pressure and may be measured in order to determine the force of contact between the probe and the tissue. On the other hand, the width of the helical cut may be chosen so as to inhibit bending of the distal tip beyond a certain angular limit in order to avoid damaging the probe.

There is therefore provided, in accordance with an embodiment of the present invention, a medical probe, including:
a flexible insertion tube, having a distal end for insertion into a body cavity of a patient;
a distal tip, which is disposed at the distal end of the insertion tube and is configured to be brought into contact with tissue in the body cavity; and
a coupling member, which couples the distal tip to the distal end of the insertion tube and includes a tubular piece of an elastic material having a helical cut therethrough along a portion of a length of the piece.

In a disclosed embodiment, the elastic material includes a superelastic alloy, and the helical cut subtends an angle between 360° and 720° about an axis of the tubular piece.

Typically, the coupling member is configured to bend in response to pressure exerted on the distal tip when the distal tip engages the tissue, and the helical cut has a width chosen so as to inhibit bending of the distal tip beyond a predetermined angular limit.

In some embodiments, the probe includes a position sensor within the distal tip, wherein the position sensor is configured to sense a position of the distal tip relative to the distal end of the insertion tube, which changes in response to deformation of the coupling member. In a disclosed embodiment, the position sensor is configured to generate a signal in response to a magnetic field, wherein the signal is indicative of a position of the distal tip. The probe may include a magnetic field generator within the distal end of the insertion tube for generating the magnetic field. Additionally or alternatively, the probe includes an electrical conductor, which is coupled to a distal side of the position sensor and is curved to pass in a proximal direction around the position sensor and through the insertion tube so as to convey position signals from the position sensor to a proximal end of the insertion tube.

In some embodiments, the probe includes a pull-wire for use by an operator of the probe in steering the probe, wherein the pull-wire passes through the insertion tube and is anchored at a point in the distal end of the insertion tube that is proximal to the helical cut in the coupling member. Alternatively or additionally, the probe includes a heat-resistant plastic sheath covering at least the coupling member.

In a disclosed embodiment, the insertion tube, distal tip and coupling member are configured for insertion through a blood vessel into a heart of a patient.

There is also provided, in accordance with an embodiment of the present invention, a method for performing a medical procedure, including:
inserting into a body cavity of a patient a probe, which includes a flexible insertion tube and a distal tip, which is disposed at a distal end of the insertion tube, and a coupling member, which couples the distal tip to the distal end of the insertion tube and includes a tubular piece of an elastic material having a helical cut therethrough along a portion of a length of the piece; and
bringing the distal tip into contact with tissue in the body cavity.

In a disclosed embodiment, inserting the probe includes passing the probe through a blood vessel into a heart of the patient, and the method includes ablating the tissue with which the distal tip is in contact.

There is additionally provided, in accordance with an embodiment of the present invention, a method for producing a medical probe, including:
providing a flexible insertion tube, having a distal end for insertion into a body cavity of a patient, and a distal tip, which is configured to be brought into contact with tissue in the body cavity; and coupling the distal dip to the distal end of the insertion tube using a coupling member, which includes a tubular piece of an elastic material having a helical cut therethrough along a portion of a length of the piece.

The present invention will be more fully understood from the following detailed description of the embodiments thereof, taken together with the drawings in which:

BRIEF DESCRIPTION OF THE DRAWINGS

FIG. 3 is a schematic side view of a coupling member, in accordance with an embodiment of the present invention.

DETAILED DESCRIPTION OF EMBODIMENTS

Figure 1:
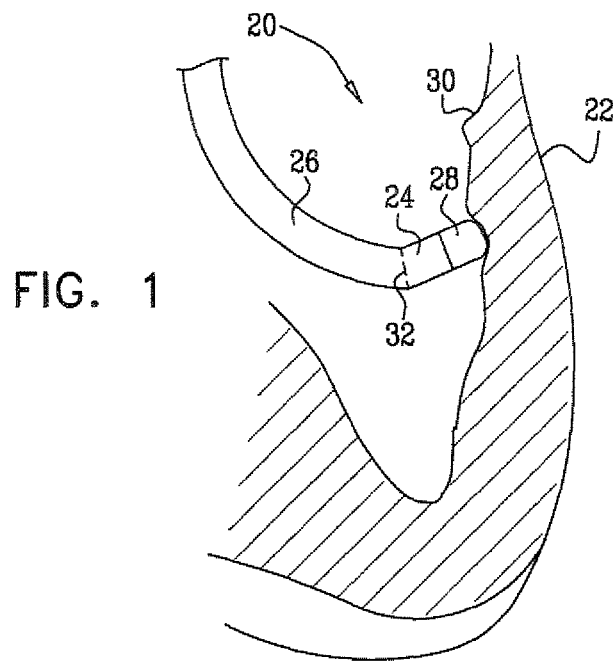
FIG. 1 is a schematic sectional view of a heart chamber with a catheter in contact with the heart wall inside the chamber, in accordance with an embodiment of the present invention.

FIG. 1 is a schematic sectional view of a chamber of a heart 22, showing an insertion tube 26 of a catheter 20 inside the heart, in accordance with an embodiment of the present invention. The catheter is typically inserted into the heart percutaneously through a blood vessel, such as the vena cava or the aorta. An electrode 28 on a distal tip 24 of the catheter engages endocardial tissue 30. Pressure exerted by the distal tip against the endocardium deforms the endocardial tissue locally, so that electrode 28 contacts the tissue over a relatively large area. In the pictured example, the electrode engages the endocardium at an angle, rather than head-on. Distal tip 24 therefore bends at an elastic joint 32 relative to the insertion tube of the catheter. The bend facilitates optimal contact between the electrode and the endocardial tissue.

Because of the elastic quality of joint 32, the angle of bending of the joint is proportional to the pressure exerted by tissue 30 on distal tip 24 (or equivalently, the pressure exerted by the distal tip on the tissue). Measurement of the bend angle thus gives an indication of this pressure. The pressure indication may be used by the operator of catheter 20 is ensuring that the distal tip is pressing against the endocardium firmly enough to give the desired therapeutic or diagnostic result, but not so hard as to cause undesired tissue damage. U.S. patent application Ser. No. 11/868,733, filed Oct. 8, 2007, whose disclosure is incorporated herein by reference, describes a system that uses a pressure-sensing catheter in this manner. Catheter 20 may be used in such a system.

Figure 2:
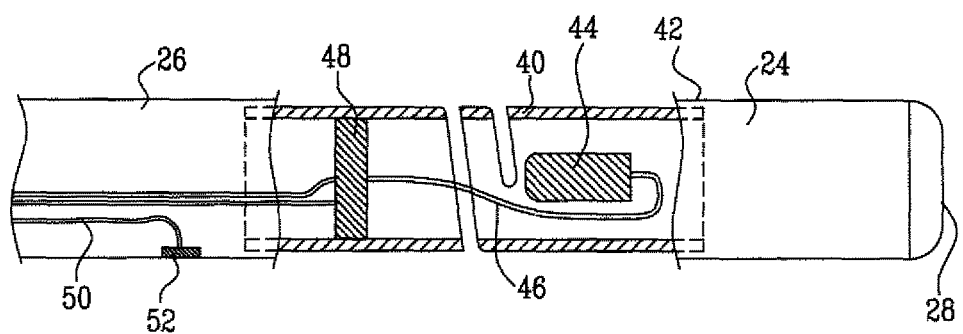
FIG. 2 is a schematic sectional view of a catheter, in accordance with an embodiment of the present invention.

FIG. 2 is a schematic, sectional view of catheter 20, showing details of the distal end of the catheter, in accordance with an embodiment of the present invention. A coupling member 40 forms the joint between distal tip 24 and the distal end of insertion tube 26. The coupling member has the form of a tubular piece of an elastic material, with a helical cut along a portion of its length, as shown more particularly in FIG. 3. Typically, the coupling member (along with the distal end of catheter 20 generally) is covered by a flexible plastic sheath 42. When catheter 20 is used, for example, in ablating endocardial tissue by delivering RF electrical energy through electrode 28, considerable heat is generated in the area of distal tip 24. For this reason, it is desirable that sheath 42 comprise a heat-resistant plastic material, such as polyurethane, whose shape and elasticity are not substantially affected by exposure to the heat.

Catheter 20 comprises a position sensor 44 within distal tip 24. (In the pictured embodiment, the position sensor is contained within a part of coupling member 40 that is inside the distal tip of the catheter.) The position sensor is connected via a conductor 46 to a processing unit (not shown) at the proximal end of insertion tube 26. Conductor 46 may typically comprise a twisted-pair cable. Position sensor 44 is configured to sense the position of the distal tip relative to the distal end of the insertion tube. As explained above, this position changes in response to deformation of the coupling member, and the processing unit may thus use the position reading in order to give an indication of the pressure exerted on and by the distal tip.

For intracardiac operation, insertion tube 26 and distal tip 24 should generally have a very small outer diameter, typically on the order of 2-3 mm. Therefore, all of the internal components of catheter 20, such as conductor 46, are also made as small and thin as possible and are thus susceptible to damage due to even small mechanical strains. To avoid damage to conductor 46 when coupling member 40 bends, the conductor is coupled to the distal side of position sensor 44, as shown in FIG. 2, rather than to the proximal side, from which the path of the conductor would be shorter. The conductor is then curved to pass in a proximal direction around the position sensor and through insertion tube 26 so as to convey position signals from the position sensor to the processing unit via the proximal end of the insertion tube.

Position sensor 44 may comprise one or more coils, which are configured to generate signals in response to a magnetic field. These signals are indicative of the position and orientation of distal tip 24. The magnetic field may be produced by a miniature magnetic field generator 48 within the distal end of the insertion tube. Thus, when coupling member 40 bends, the signals generated by the position sensor change and can be analyzed by the processing unit to determine the pressure on the distal tip. Additional magnetic fields may be generated by field generators (not shown) in fixed locations external to the patient's body. These fields cause position sensor 44 to generate additional signals that are indicative of the position and orientation of distal tip 24 in the fixed frame of reference of the external field generators. These aspects of the operation of position sensor 44 are described in detail in the above-mentioned U.S. patent application Ser. No. 11/868,733. They are outside the scope of the present invention.

Catheter 20 may comprise a pull-wire 50 for use by an operator in steering the catheter. The pull-wire passes through insertion tube 26 and is anchored at an anchor point 52 in the distal end of the insertion tube. The operator tightens the pull-wire (typically by turning a knob—not shown—at the proximal end of the catheter) in order to bend the distal end of the catheter. When the operator releases the pull-wire, the catheter straightens due to the resilience of the insertion tube. In catheters that are known in the art, the pull-wire is anchored near the distal tip of the catheter. In catheter 20, however, anchor point 52 is proximal to the helical cut in coupling member 40, and may be proximal to the coupling member altogether, as shown in FIG. 2. This relatively proximal positioning of the anchor point means that the pull-wire steers the catheter as a whole, rather than bending the coupling member and distal tip.

FIG. 3 is a schematic side view of coupling member 40, in accordance with an embodiment of the present invention. As noted earlier, the coupling member comprises a tubular piece 60 of an elastic material, typically a metal material. For example, the coupling member may comprise a superelastic alloy, such as nickel titanium (NITINOL™). For intracardiac applications, the tube 60 may typically have a length of 10 mm, with outer diameter 2.0 mm and wall thickness 0.05 mm. Alternatively, in other applications, the tube 60 may have larger or smaller dimensions.

A helical cut 62 is made along a portion of the length of tubular piece 60, and thus causes the tubular piece to behave like a spring in response to forces exerted on distal tip 24. Cut 62 may be made by laser machining of the tubular piece. For the tube dimensions given above, cut 62 is typically opened by the laser to a width of about 0.1 mm. To give the appropriate balance between flexibility and stiffness for intracardiac applications, cut 62 typically subtends an angle between 360° and 720° about the central axis of the tubular piece, as illustrated in FIG. 3 (in which the cut subtends about 540°). Alternatively, larger or smaller angular extents may be used depending on application requirements.

The spring-like behavior of coupling member 40 extends up to a certain angle of bending of tubular piece 60, for example, 30°. Above this angle, the sides of cut 62 on the inner side of the bend will come into contact, thereby inhibiting any further bending of the distal tip. The width of the cut may thus be chosen so as to impose a predetermined angular limit on the bending of joint 32 (FIG. 1). This sort of bend limit is useful in preventing damage that may occur to the delicate internal components of catheter 20 due to excessive bending.

Although the operation and construction of catheter 20 are described above in the context of catheter-based intracardiac procedures, the principles of the present invention may similarly be applied in other therapeutic and diagnostic applications that use invasive probes, both in the heart and in other organs of the body. Furthermore, the principles of the implementation of catheter 20 and coupling member 40 may also be applied to enhance flexibility in catheter designs of other types, such as lasso, helix, and "Pentarray" type catheters. In a helical lasso catheter, for example, resilient elements like coupling member 40 may be incorporated in the helix in order to enhance the ease of use and accuracy of alignment of the lasso in the desired position within the heart.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for performing a medical procedure, comprising:
   inserting into a body cavity of a patient a probe, which comprises a flexible insertion tube and a distal tip, which is disposed at a distal end of the insertion tube, a coupling member that couples the distal tip to the distal end of the insertion tube and comprises a tubular piece of an elastic material having a helical cut therethrough along a portion of a length of the piece, a position sensor within the distal tip, the position sensor being configured to generate a signal in response to a magnetic field, wherein the signal is indicative of a position of the distal tip, and a magnetic field generator within the distal end of the insertion tube for generating the magnetic field;
   generating the magnetic field;
   generating the signal in response to the magnetic field;
   analyzing the signal to determine if the distal tip is pressing against the tissue in the body cavity firmly to give the desired therapeutic or diagnostic result without causing undesired tissue damage; and
   if the distal tip is not pressing against the tissue in the body cavity firmly to give the desired therapeutic or diagnostic result without causing undesired tissue damage, repositioning the distal tip to bring the distal tip into contact with tissue in the body cavity.

2. The method according to claim 1, wherein inserting the probe comprises passing the probe through a blood vessel into a heart of the patient.

3. The method according to claim 1, further comprising ablating the tissue with which the distal tip is in contact.

4. The method according to claim 1 wherein the coupling member comprises a tubular piece of a superelastic alloy.

\* \* \* \* \*